United States Patent [19]

Itor et al.

[11] Patent Number: 4,814,353
[45] Date of Patent: Mar. 21, 1989

[54] THERAPEUTIC AND PROPHYLACTIC AGENT FOR GASTRITIS

[75] Inventors: Masaharu Itor; Kiyokazu Tsujide, both of Tokyo, Japan

[73] Assignee: Eisai Co., Ltd., Tokyo, Japan

[21] Appl. No.: 878,469

[22] Filed: Jun. 25, 1986

[30] Foreign Application Priority Data

Jul. 4, 1985 [JP] Japan ................................. 60-145757

[51] Int. Cl.$^4$ ............................................. A61K 31/12
[52] U.S. Cl. .................................................... 514/675
[58] Field of Search ......................................... 514/675

[56] References Cited

U.S. PATENT DOCUMENTS 4,169,157 9/1979 Kijima et al. ..................... 514/675

Primary Examiner—Frederick E. Waddell
Attorney, Agent, or Firm—Flynn, Thiel, Boutell & Tanis

[57] ABSTRACT

Gastritis is treated and prevented by administration to a human being of a prenyl ketone compound having the formula in which n is 3, 4 or 5.

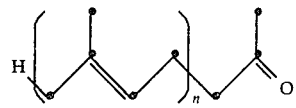

4 Claims, No Drawings

THERAPEUTIC AND PROPHYLACTIC AGENT FOR GASTRITIS

The present invention relates to a therapeutic and prophylactic agent for gastritis, and more specifically to a therapeutic and prophylactic agent for gastritis comprising as the effective ingredient a prenyl ketone compound represented by the following chemical formula:

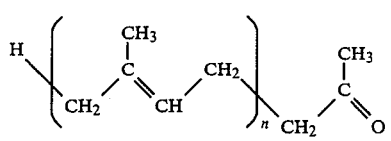
(I)

(wherein n represents an integer of 3 to 5).

The invention provides a method for treating and preventing gastritis, which comprises administering to a patient suffering from the gastritis or a human being a therapeutically effective amount of a prenyl ketone compound having the above defined formula.

Moreover the invention provides the use of a prenyl ketone compound having the formula for treatment and prevention of gastritis.

In addition the invention provides the use of a prenyl ketone compound having the formula for preparation of a therapeutic and prophylactic agent against gastritis.

Gastritis is not necessarily clear in the special definition thereof in view of the fact that it is usually divided into acute gatritis and chronic gastritis in the discussion thereof. In the present invention, the term is used as including both types of gastritis.

Chronic gastritis is usually classified into superficial gastritis and atrophic gastritis, and further into atrophic hyperplastic gastritis, hypertrophic gastritis, etc. A sign common thereto is chronic inflammatory lesion of tunica mucosa ventriculi. The symptom is inconstant compliant in epigastrium in most cases. Specifically, representative examples of the symptom include anorexia, esophagostenosis, pyrosis, nausea, emesis, epigastrium dysphoria, epigastralgia, and flatulence.

Acute gastritis is generally inflammatory lesion of tunica mucosa ventriculi rapidly caused by an endogenous or xenogenic stimulus, and is usually accompanied by erosion.

The inventors of the present invention previously studied polyprenyl compounds, and found that the compound according to the present invention was effective against various peptic ulcers as disclosed in U.S. Pat. No. 4,169,157 and corresponding U.K. Pat. No. 1,602,566.

Subsequently, the inventors of the present invention have intensively studied on the drug efficacy of the compound according to the present invention over long years, and have unexpectedly found that the compound according to the present invention is effective in therapy and prophylaxis of gastritis. The present invention has been completed based on this finding.

Accordingly, an object of the present invention is to provide a novel therapeutic and prophylactic agent.

The compound according to the present invention is a prenyl ketone compound represented by the general formula (I):

(I)

(wherein n represents an integer of 3 to 5). Among polyprenyl ketone compounds with n=3 to 5, the most preferred and representative compound is 6,10,14,18-tetramethyl-5,9,13,17-nonadecatetraen-2-one with n=4 which has the following formula (II):

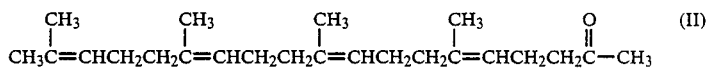
(II)

Various isomers are conceivable in the compound according to the present invention as is apparent from the structure thereof. The present invention involves all of them.

In the case of 6,10,14,18-tetramethyl-5,9,13,17-nonadecatetraen-2-one with n=4 which has the above-mentioned formula (II), various isomers are, of course, conceivable. The present invention involves all of them. Specific examples of them include (5E,9E,13E)-6,10,14,18-tetramethyl-5,9,13,17-nonadecatetraen-2-one and (5Z,9E,13E)-6,10,14,18-tetramethyl-5,9,13,17-nonadecatetraen-2-one. The present invention, of course, further involves mixtures of these isomers.

A 3:2 mixture of (5E,9E,13E)-6,10,14,18-tetramethyl-5,9,13,17-nonadecatetraen-2-one and (5Z,9E,13E)-6,10,14,18-tetramethyl-5,9,13,17-nonadecatetraen-2-one, which is one embodiment of the compound according to the present invention, has the following properties.

molecular formula: $C_{23}H_{38}O$
molecular weight: 330.55
physicochemical properties: a colorless to slightly yellowish, transparent, oily liquid having a slight peculiar odor and no taste, which is hardly soluble in water but soluble in organic solvents.
refractive index $n_D^{20}$: 1.485 to 1.491
specific refractive index $n_{20}^{20}$: 0.882 to 0.890

The compound according to the present invention can be prepared in accordance with the process described in the above shown U.S. patent and U.K. patent.

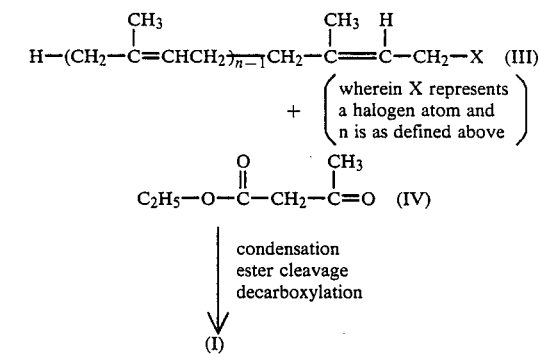

More specifically, a prenyl halide represented by the formula (III) is condensed with ethyl acetoacetate represented by the formula (IV) in the presence of a condensation agent such as metallic sodium, metallic potassium, sodium ethylate, or sodium hydrate and, if necessary, in a solvent such as ethanol, t-butanol, dioxane, or benzene, and the resulting product is treated with an alkaline reagent such as a dilute aqueous sodium hydroxide solution or a dilute aqueous potassium hydroxide solution to effect ester cleavage and decarboxylation. Thus, the desired compound can be obtained.

The desired compound can also be prepared by the following process.

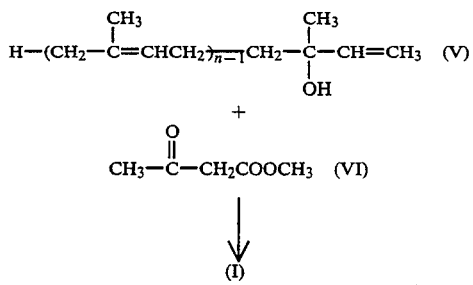

Specifically, a prenyl alcohol represented by the formula (V) and methyl acetoacetate represented by the formula (VI) are subjected to the Carroll reaction in a customary manner to obtain a desired product (I). In the case of n=4, geranyllinalool and methyl acetoacetate are subjected to the Carroll reaction in a customary manner.

Specific clinical instances will be illustrated to substantiate the effect of the present invention. In the clinical instances, "teprenone" refers to a compound according to the present invention (teprenone is 6,10,14,18-tetramethyl-;b 5,9,13,17-nonadecatetraen-2-one with n=4 in the general formula (I)).

CLINICAL INSTANCE 1

19-year old female: actute gastritis

The instance is concerned with a female who visited a hospital while mainly complaining of epigastralgia. Lesion of tunica mucosa ventriculi was recognized in the vestibulum (paries anterior ventriculi, curvatura ventriculi minor, paries posterior ventriculi, curvatura ventriculi major), and hence diagnosed as acute gastritis.

The subjective symptoms included not only severe epigastralgia but also medium nausea, emesis, anorexia, slight pyrosis, abdominal flatulence, abdominal oppression, gastric dysphoria, and eructation.

150 mg per day of teprenone, which is a compound according to the present invention, was perorally administered to the patient. 3 days after the administration, all the symptons disappeared. In endoscopy carried out 5 days after the administration, disappearance of the lesion of the tunica mucosa ventriculi was recognized.

There were no side effect altogether, and no abnormality was recognized in the observation of clinical inspection.

CLINICAL INSTANCE 2

64-year old female: acute animus state of chronic gastritis

The conditions of the patient before administration were as follows.

The patient complained of subjective symptoms including severe pyrosis, eructation, and slight nausea and emesis. Lesion of mucosa ventriculi was endoscopically recognized in the curvature ventriculi major of the vestibulum.

150 mg per day of teprenone, which is the compound according to the present invention, was perorally administered to the patient. 3 days after the administration, all the symptoms disappeared. In endoscopy carried out 16 days after the administration, disappearance of the lesion of tunica mucosa ventriculi was recognized.

No side effects were recognized altogether even in the observation of clinical inspection.

CLINICAL INSTANCE 3

26-year old male: acute gastritis

The conditions of te patient before administration were as follows.

The subjective symptoms included severe epigastralgia, anorexia, medium pyrosis, nausea, emesis, abdominal flatulence, gastric dysphoria, slight abdominal oppression, and eructation.

In endoscopy before administration, lesion of tunica mucosa ventriculi was recognized in the vestibulum (paries anterior venticuli, curvatura ventriculi minor, paries posterior ventriculi) and angularis (paries anterior ventriculi, curvatura ventriculi minor, paries posterior ventriculi).

150 mg per day of teprenone, which is the compound according to the present invention, was perorally administered to the patient. 3 days after the administration, all the symptoms disappeared. In endoscopy carried out 5 days after the administration, disappearance of the lesion of tunica mucosa ventriculi was recognized.

There were no side effects altogether, and no lesion was recognized in the observation of clinical inspection.

CLINICAL INSTANCE 4

20-year old female: acute animus stage of chronic gastritis

The conditions of the patient before administration were as follows. The patient complained of medium epigastralgia, slight abdominal oppression, gastric dysphoria, and anorexia. Lesion of tunica mucosa ventriculi was endoscopically recognized in the curvatura ventriculi minor of the angularis and the curvatura ventriculi minor of the corpus ventriculi.

150 mg per day of teprenone, which is the compound according to the present invention, was perorally administered to the patient. 3 days after the administration, substantially all the symptoms disappeared except that slight epigastralgia remained. 5 days after the administration, the epigastralgia also disappeared.

In endoscopy carried out 14 days after the administration, disappearance of the lesion of tunica mucosa ventriculi was recognized.

No side effects were recognized altogether even in the observation of clinical inspection.

CLINICAL INSTANCE 5

18-year old male: acute animus stage of chronic gastritis

The conditions of the patient before administration were as follows.

The subjective symptoms included epigastralgia, pyrosis, abdominal oppression, gastric dysphoria, and eructation. The levels of them were all medium.

Endoscopically, lesion was recognized in the vestibulum (paries anterior ventriculi, curvatura ventriculi minor, paries posterior ventriculi).

150 mg per day of teprenone, which is the compound according to the present invention, was perorally administered to the patient. 3 days after the administration, the abdominal oppression, the gastric dysphoria, and the eructation were mitigated, but the epigastralgia and the pyrosis remained unchanged. A week after the administration, all the symptoms disappeared except for slight eructation. The eructation remained even after two weeks.

In endoscopy carried out after two weeks, the lesion of tunica mucosa ventriculi disappeared in all parts.

No side effects were regonized.

The results of the toxicity test of the compound according to the present invention are listed in Table 1.

TABLE 1

| Animal species | Sex | Acute Toxicity $LD_{50}$ (mg/μg) | | | |
|---|---|---|---|---|---|
| | | Peroral | Intra-muscular | Sub-cutaneous | Intra-peritoneal |
| mouse (ICR) | ♂ | >15,000 | >5,000 | >10,000 | 3,750 |
| | ♀ | >15,000 | >5,000 | >10,000 | 3,850 |
| rat (SD) | ♂ | >15,000 | >5,000 | >10,000 | >5,000 |
| | ♀ | >15,000 | >5,000 | >10,000 | 5,000~3,500 |
| dog (beagle) | ♂ | >1,000 | — | — | — |
| | ♀ | >1,000 | — | — | — |

The compound according to the present invention is effective in therapy and prophylaxis of acute and chronic gastritis as is apparent from the above-mentioned clinical instances.

Furthermore, as is apparent from the results of the toxicity test, the compound according to the present invention is very highly safe. Thus, no problems occur even in the case of chronic gastritis which requires repeated administration for a long period of time. Also, in this sense, the merit of the present invention is great.

The compound according to the present invention is administered either perorally in the form of a powder, tablets, granules, capsules, balls, a solution, or the like, or parenterally in the form of an injection, a suppository, or the like.

Although the dosage is not particularly limitative since it is different depending on the age and symptom of a patient, it is about 20 to 20,000 mg, preferably about 50 to 1,000 mg, still preferably about 100 to 500 mg, per day for adults, which is administered in portions of two to four times a day.

The compound according to the present invention can be dispensed for administration by any arbitrary customary pharmacy. Accordingly, the present invention also involves a preparation composition containing at least one compound according to the present invention suitable as the medicine for the human body. Such a composition is used with the aid of an arbitrary and necessary pharmaceutical carrier or excipient according to a customary method.

The composition is preferably provided in a form suitable for absorption thereof from a digestive tract. Tablets and capsules for peroral administration are in the administrative form of unit dosage, and may contain common additives selected from among binders such as syrup, gum arabic, gelatin, sorbitol. tragacanth, and polyvinylpyrrolidone; excipients such as lactose, maize starch, calcium phosphate, sorbitol, and glycine; lubricants such as magnesium stearate, talc, polyethylene glycol, and silica; disintegrators such as potato starch; and acceptable wetting agents such as sodium lauryl sulfate. Tablets may be coated by a method known in the art. A peroral liquid preparation may be in the form of an aqueous or oily suspension, a solution, a syrup, an elixir, or the like, or may be a dry product capable of being redissolved in water or other adequate vehicle before use thereof. The liquid preparation may contain a common additive(s) selected from among suspending agents such as sorbitol syrup, methylcellulose, glucose/sugar syrup, gelatin, hydroxyethylcellulose, carboxymethylcellulose, aluminum stearate gel, and edible hydrogenated fats; emulsifiers such as lecithin, sorbitan monooleeate, and gum arabic; non-aqueous vehicles such as almond oil, fractionated coconut oil, oily esters, propylene glycol, and ethyl alcohol; and preservatives such as methyl p-hydroxybenzoate, propyl p-hydroxybenzoate, and sorbic acid.

An injection composition is provided in ampules of unit dosage or containers of multiple dosages with an additive preservative. The composition may be in the form of a suspension, a solution, or an emulsion of an oily or aqueous vehicle type, and may contain a formulating ingredient such as a suspending agent, a stabilizer, and/or a dispersant. On the other hand, the active ingredient may be in the form of a powder capable of being re-dissolved in an adequate vehicle such as sterilized water containing no pyrogens.

Preparation examples in embodying the present invention will now be described.

PREPARATION EXAMPLE 1

| Capsule | |
|---|---|
| 6,10,14,18-tetramethyl-5,9,13,17-nonadecatetraen-2-one | 5 g |
| microcrystalline cellulose | 80 g |
| corn starch | 20 g |
| lactose | 22 g |
| polyvinylpyrrolidone | 3 g |
| total amount | 130 g |

The above-mentioned ingredients were formed into granules by a customary method, and filled in 500 hard gelatin capsules. 10 mg of the base was contained in one capsule.

PREPARATION EXAMPLE 2

| Powder | |
|---|---|
| 6,10,14,18,22-pentamethyl-5,9,13,17,21-tricosapentaen-2-one | 50 g |
| microcrystalline cellulose | 400 g |
| corn starch | 550 g |
| total amount | 1,000 g |

The base was dissolved in acetone, and then absorbed in microcrystalline cellulose, followed by drying. The mixture was further mixed with corn starch or maize starch and formed to powder by a conventional method to prepare a powder having the base diluted 20-fold.

PREPARATION EXAMPLE 3

| Tablet | |
|---|---|
| 6,10,14,18-tetramethyl-5,9,13,17-nonadecatetraen-2-one | 5 g |

|  |  |
|---|---|
| corn starch | 10 g |
| purified saccharose | 20 g |
| calcium carboxymethylcellulose | 10 g |
| microcrystalline cellulose | 40 g |
| polyvinylpyrrolidone | 5 g |
| talc | 10 g |
| total amount | 100 g |

The base was dissolved in acetone, and then absorbed in microcrystalline cellulose, followed by drying. The resulting mixture was admixed with maize starch, purified saccharose, and calcium carboxymethylcellulose, followed by addition of an aqueous polyvinylpyrrolidone solution as the binder. The resulting mixture was formed into granules by a customary method. Talc was admixed as the lubricant with the granules, and formed into a tablet of 200 mg. One tablet contained 10 mg of the base.

PREPARATION EXAMPLE 4

| Hard Capsule | |
|---|---|
| 6,10,14-trimethyl-5,9,13-pentadecatrien-2-one | 50 g |
| BHA | 0.05 g |
| microcrystalline cellulose | 800 g |
| corn starch | 200 g |
| lactose | 220 g |
| polyvinylpyrrolidone | 30 g |

Granules were formed by a customary method. 100 mg each of granules were filled in a hard capsule No. 4.

PREPARATION EXAMPLE 5

| Tablet | |
|---|---|
| 6,10,14,18-tetramethyl-5,9,13,17-nonadecatetraen-2-one | 5 g |
| corn starch | 10 g |
| lactose | 20 g |
| calcium carboxymethylceluose | 10 g |
| microcrystalline cellulose | 40 g |
| polyvinylpyrrolidone | 5 g |
| talc | 10 g |
| natural tocopherol | 0.025 g |

The base was dissolved in acetone, admixed with natural tocopherol, and then absorbed in microcrystalline cellulose, followed by drying. The resulting mixture was mixed with maize starch, lactose, and calcium carboxymethylcellulose, followed by formation of granules with the aid of a methanol solution of polyvinylpyrrolidone. The talc was added to the granules, and the resulting mixture was formed into a tablet of 200 mg.

PREPARATION EXAMPLE 6

| Injection | |
|---|---|
| 6,10,14,18-tetramethyl-5,9,13,17-nonadecatetraen-2-one | 10 g |
| dl-α-tocopherol | 0.01 g |
| Nikkol HCO 60 | 50 g |
| sesame oil | 2 g |
| sodium chloride | 9 g |
| propylene glycol | 40 g |
| phosphate buffer solution (0.1 M, pH: 6.0) | 100 ml |
| distilled water total amount | 1,000 ml |

The base, dλ,α-tocopherol, Nikkol HCO 60, sesame oil, and half of a necessary amount of propylene glycol were mixed together and heated at 80° C. to effect dissolution. The resulting solution was admixed with a phosphate buffer solution, sodium chloride, and remaining propylene glycol which were separately and preliminarily dissolved in part of distilled water and heated at 80° C. Distilled water was added to the resulting mixture to 1,000 ml. The resulting solution was filled in 2 ml ampules, which were then melt-sealed and sterilized at 120° C. for 30 minutes.

The embodiments of the invention in which an exclusive property or privilege is claimed are defined as follows:

1. A method for treating gastritis, which comprises administering to a patient suffering from gastritis a therapeutically effective amount of a prenyl ketone compound having the formula:

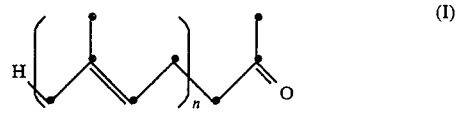

(I)

in which n is 3, 4 or 5.

2. A method as claimed in claim 1, in which n is 3.
3. A method as claimed in claim 1, in which n is 4.
4. A method as claimed in claim 1, in which n is 5.

* * * * *